(12) United States Patent
Ginggen

(10) Patent No.: US 6,658,281 B2
(45) Date of Patent: *Dec. 2, 2003

(54) MINI-INVASIVE NUCLEAR MAGNETIC RESONANCE SPECTROSCOPY CATHETER PROBE

(75) Inventor: Alec Ginggen, Muntschemier (CH)

(73) Assignee: Medos S.A. (CH)

( * ) Notice: Subject to any disclaimer, the term of this patent is extended or adjusted under 35 U.S.C. 154(b) by 15 days.

This patent is subject to a terminal disclaimer.

(21) Appl. No.: 09/797,819

(22) Filed: Mar. 2, 2001

(65) Prior Publication Data

US 2001/0029332 A1 Oct. 11, 2001

(30) Foreign Application Priority Data

Mar. 6, 2000 (CH) .............................. 00104773

(51) Int. Cl.[7] .............................. A61B 5/05; A61B 6/00
(52) U.S. Cl. .................. 600/419; 600/415; 600/431; 324/308; 324/312
(58) Field of Search .................. 600/109, 413, 600/415, 419, 421, 422, 431, 411, 521; 604/175; 436/173; 424/9.3, 9.32, 9.37; 324/306–309, 312, 321, 322, 201, 204

(56) References Cited

U.S. PATENT DOCUMENTS

| | | | | |
|---|---|---|---|---|
| 5,035,231 A | * | 7/1991 | Kubokawa et al. | 600/109 |
| 5,072,732 A | * | 12/1991 | Rapoport et al. | 600/415 |
| 5,314,450 A | | 5/1994 | Thompson | |
| 5,479,925 A | * | 1/1996 | Dumoulin et al. | 600/419 |
| 5,959,453 A | * | 9/1999 | Taicher et al. | 600/410 |

FOREIGN PATENT DOCUMENTS

EP 377695 B1 11/1989

* cited by examiner

Primary Examiner—Tu Ba Hoang
(74) Attorney, Agent, or Firm—Eugene L. Szczecina, Jr.

(57) ABSTRACT

Nuclear magnetic resonance spectroscopy catheter probe comprising a permanent magnet arrangement (1,2,3,4) for generating a static magnetic field of suitable intensity and homogeneity for analysing a sample of fluid flowing into a catheter (6) traversing the permanent magnet arrangement. The probe further comprises an arrangement of electronic circuits (8,9) responsible for the excitation and detection of the nuclear magnetic resonance signal and at least one coil (7) to expose the fluid sample to the excitation signal and to collect the returned nuclear magnetic resonance signal.

12 Claims, 1 Drawing Sheet

MINI-INVASIVE NUCLEAR MAGNETIC RESONANCE SPECTROSCOPY CATHETER PROBE

BACKGROUND

The present invention relates to a catheter probe, more particularly to a catheter probe comprising a magnetic nuclear resonance spectrometer arrangement capable of characterising and monitoring the local flow rate of a physiological fluid as well as its chemical composition.

Nuclear magnetic resonance is based on the following known principle. All atomic nuclei with an odd atomic mass or an odd atomic number (like hydrogen for example) possess an intrinsic nuclear magnetic momentum. Without entering the details, one can consider that this momentum is generated by the rotation of the proton around the nucleus. When a NMR active nucleus is placed in a static magnetic field, this momentum can take two different orientations. The momentum may take either an orientation parallel to the magnetic field or an antiparallel orientation relative to the magnetic filed. Considering a population of hydrogen atoms immersed in the same static magnetic field, the number of atoms having a parallel orientation is slightly greater than the number of atoms having an anti-parallel orientation. This is due the fact that the parallel orientation is energetically more favourable. The passage from the parallel state to the anti parallel state occurs when the atoms absorb electromagnetic energy at a given frequency called the resonance frequency. This resonance frequency depends on the nucleus of the atom and on the intensity of the static magnetic field. A magnetic nuclear resonance apparatus works by analysing the signal emitted during the transition from the excited state (anti-parallel) to the state of equilibrium (parallel). The nuclei are placed in a high intensity static magnetic field and then exited with an electromagnetic wave having a frequency corresponding to the resonance frequency. When the return to the equilibrium state occurs, a signal having the same frequency as the excitation signal (resonance) is generated and can be measured thanks to an antenna.

The resonance detection may occur either at the stage of excitation, by measuring the energy absorption by scanning a range of frequency or when the atoms return to the state of equilibrium. In the later, one measures the electromagnetic signal emitted by the magnetic momentum returning to their equilibrium position. If other atoms than hydrogen atoms are present in the solution to be characterised, the spin of their electrons will generate a magnetic field at the microscopic level. Thus the hydrogen atoms are submitted to the static magnetic field generated by the NMR device to which is superposed locally the magnetic field generated by the electrons. This will alter the resonance frequency with a signature specific to the environment of the hydrogen atoms within the solution to characterise. Nuclear magnetic resonance spectroscopy is based on this principle and is mainly used for two different kind of applications, namely for biochemical analysis in laboratories and in magnetic resonance imaging spectroscopy. In laboratories, nuclear magnetic resonance spectroscopy is usually performed at very high magnetic field intensity (>10 Tesla) to reveal the atomic structure of molecules. In contrast magnetic resonance imaging spectroscopy (MRIS) is performed with standard MRI equipment at lower filed intensity (around 1.5 Tesla) to reveal the composition of the tissues environment at molecular level.

It is also possible to gather information related to the flow of a liquid by analysing the signal returning to the equilibrium state after a resonant excitation. This signal has a decrease, which is characteristic when the liquid is static, and a faster decrease when the liquid is in movement. This is due to the fact that part of the excited atoms will leave the detection volume of the antenna. This technique also used in magnetic resonance imaging spectroscopy devices.

Chronic monitoring of specific chemical compounds in a body fluid as well as gathering information relative to the flow rate of a fluid within the human body is a key in many areas of medicine, this is particularly true for brain metabolites monitoring in traumatic patient or for monitoring the flow rate of the cerebrospinal fluid in a shunted hydrocephalic patient. The known techniques for monitoring the concentration of specific chemical compounds in a physiological fluid are usually achieved invasively either by techniques that require taking samples of the fluid (dialysis, . . . ) or by inserting probes in the targeted fluid/tissue (micro dialysis, blood gas analysis.) These techniques involve either a puncture for each sample to analyse or a catheter line to be left in place for the duration of the monitoring. Known invasive catheter probes are mainly targeted to specific analytes such as $O_2$, $CO_2$, glucose or lactose. Micro-dialysis is the only invasive technique that is versatile, but a continuous flow of buffer solution circulating in the catheter and solution sampling for off-line analysis is needed. The later technique can be considered as pseudo-continuous monitoring but is rather difficult to implement (requires regular sampling by qualified operator and one specific reagent per targeted analyte).

Other non-invasive techniques such as magnetic resonance imaging spectroscopy are rather expensive and do not permit a continuous monitoring. Moreover, concerning the flow rate assessment, there are currently no known devices to perform these measurements in situ.

SUMMARY OF THE INVENTION

The aim of the present invention is to remedy the aforesaid drawbacks. A mini-invasive nuclear magnetic resonance spectroscopy catheter probe having a permanent magnet, an electronics circuit, and an excitation coil connected to the electronics circuit and disposed within the probe achieves this goal.

Further features and other objects and advantages of this invention will become clear from the following detailed description made with reference to the accompanying drawings illustrating in a schematic and non-limiting way two embodiments of a nuclear magnetic resonance spectrometer probe according to the invention.

DETAILED DESCRIPTION

Figure 1:
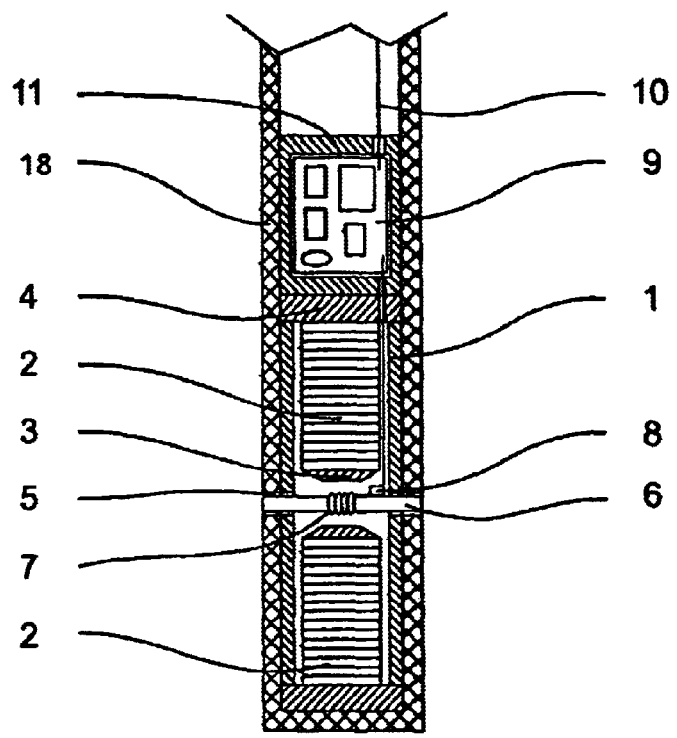
FIG. 1 is a schematic partially cross-sectional view of a first embodiment of a nuclear magnetic resonance spectroscopy catheter probe object of the present invention.

Referring to FIG. 1, there is shown a first embodiment of a nuclear magnetic resonance spectroscopy catheter probe object of the present invention. The static magnetic field is generated thanks to a permanent magnet arrangement. It is to be noted that the static magnetic field must comply with two criteria. Firstly the static magnetic field must be of high intensity. The intensity of the nuclear magnetic resonance signal is directly proportional to the number of atoms participating to the resonance, which is also directly proportional to the intensity of the magnetic field. Therefore, in order to generate a NMR signal that can be easily detected and analysed it is required to work with static magnetic field in the range of 1 Tesla and above. The second criterion that the magnetic field must fulfil is relative to its homogeneity. It is crucial that the sample to be analysed is immersed in whole in the same static magnetic field. If this is not the case, the de-excitation frequency spectrum will be broad ant thus difficult to measure and interpret. In the present case, the homogeneity of the static field should be in the range of 1–10 ppm.

A static magnetic field corresponding to these requirements is generated with an arrangement of permanent magnets located at the distal end of a catheter line. Back to FIG. 1, the arrangement of permanent magnets is constituted of a cylindrical external permanent magnet 1. The permanent magnet arrangement comprises in addition two internal permanent magnets 2 also having a cylindrical shape. The magnets 1,2 are all polarised along their longitudinal axis. The direction of the magnetisation of both internal magnets 2 is identical but in the opposed direction of the polarisation of the external magnet 1. (i.e, if the north pole of the external magnet 1 is located at the upper part of the external magnet 1, the internal magnets 2 will have their north pole toward the bottom of the figure). The magnet arrangement is completed with two magneto-concentrator 3 located on adjacent poles of the internal magnets 2. Their function is to improve the intensity and the homogeneity of the static magnetic field in the region located directly in between the two internal magnets 2. Two ferrite caps 4 are closing this magnet arrangement and thus decreasing the loss of field appearing in that region.

The external magnet 1 is provided with two central radial holes 5 allowing the passage of a catheter 6 in between the two magneto-concentrators 3 ending the internal magnets 2. The fluid to analyse will flow in the catheter 6 in the center of the magnet arrangement. An excitation/detection coil 7 is adjusted around the catheter 6 in the center of the permanent magnet structure. The volume of measure is determined by the volume of the coil which should be reduced in order to optimise the homogeneity of the field in the vicinity of the sample to analyse. Simulations have shown that homogeneity of 1 ppm is obtained with a sphere having a diameter of a 100 $\mu$m in the center of the structure for a field intensity of around 0.7 Tesla.

The excitation/detection coil 7 is connected to a electronic pre-processing circuit 8 which, in a preferred embodiment, is located as close as possible to the coil 7 in order to increase the signal to noise ratio. This pre-processing circuit 8 which detects, amplify and pre-process the NMR signal is further connected to the main printed circuit board 9 which contains all the electronic components needed for the further processing of the signal. These known components will not be described in details in the present specification but their main function can be summarised as follows. The main printed circuit board 9 comprises the necessary components to generate the nuclear magnetic resonance excitation signal at the resonance frequency. It further comprises the required components to analyse and to format the signal detected by the pre-processing circuit 8. The main circuit board 9 is connected by a connection wire 10 to an external monitoring unit (not shown). This external unit may be used to further process and to graphically represent the spectrum of the measured analytes.

The electronic circuit board 9 is enclosed in a watertight housing 11 provided with tight passages for connecting the wire 10 to an external monitoring unit and for the connection with the pre-processing circuit 8. This probe head is integrated at the distal end of a catheter which may be made in silicone for example. The silicone envelope of catheter 18 is provided with two apertures located in front of the internal catheter 6 so that the fluid to analyse may flow by diffusion through the catheter 6 when the probe is inserted in a place of interest in a human body.

Figure 2:
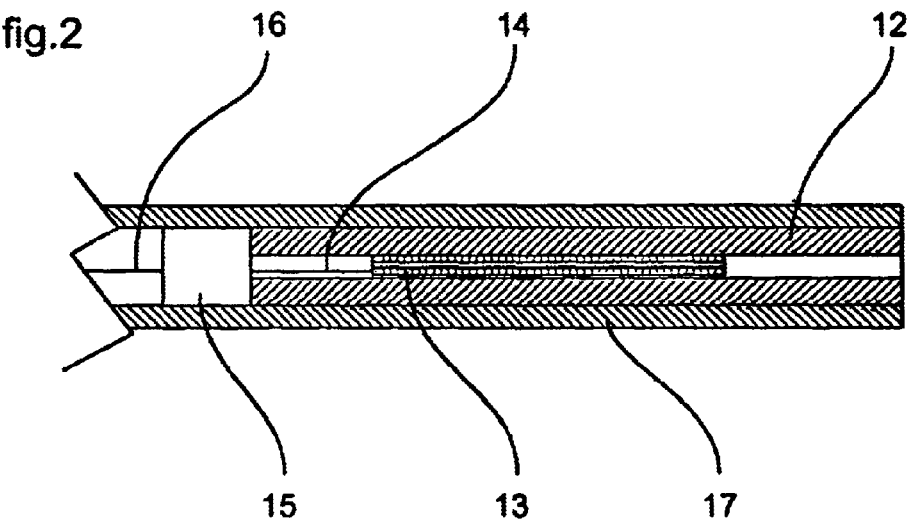
FIG. 2 is a schematic cross-sectional view of a second embodiment of a nuclear magnetic resonance spectroscopy catheter probe object of the present to invention.

FIG. 2 illustrates a second embodiment of the nuclear magnetic resonance spectroscopy catheter probe, in which the permanent magnet arrangement is constituted of cylindrical permanent magnet 12 having the structure of a cylinder of Halbach. The structures of Hallbach, based on the infinite dipole principle are known for generating very homogenous field in the center of the structure. Furthermore, in theses Halbach structures, the homogeneity of the generated magnetic field increases with the length of the magnet. Typical dimension for such a catheter probe will be approximately 150 mm in length for an overall diameter of about 3 mm. The excitation-/-detection coil 13 is located in the center of the permanent magnet 12, and connected by a wire 14 to a watertight housing 15 comprising the pre-processing circuit and the necessary electronic components used for generating the excitation signal and to format the measured data. The output of the electronic circuits contained in the housing 15 is connected with a wire 16, which extend until the proximal end of the catheter line 17, to the external monitoring unit (not shown).

The liquid to analyse will in this embodiment enter the distal end of the catheter when inserted. The circulation of the liquid in the center of the Halbach cylinder 12 is achieved by natural diffusion. It is to be noted that in this embodiment, the volume excited by the excitation coil 13 should be as large as possible to obtain better results. Thus, the excitation coil 13 extends on about $\frac{2}{3}$ of the length of the permanent magnet 12.

Due to the disclosed nuclear magnetic resonance spectroscopy catheter probe, it is possible to monitor continuously the composition and/or the concentration of specific chemical compounds in a physiological fluid. Many applications can be foreseen with this catheter probe. By way of example, the probe may be used for continuous monitoring of brain function in traumatic patients, in particular the concentration of analytes such as amino acids, glucose, glutamate, lactose, dissolved gas, etc. By providing a means to perform nuclear magnetic resonance spectroscopy locally at the distal end of a catheter, these probes allow minimally invasive continuous monitoring of any compound of interest.

What is claimed is:

1. A nuclear magnetic resonance spectroscopy catheter probe for measuring the chemical composition of a fluid or for measuring the flow rate of the fluid comprising:

a permanent magnet for generating an intense homogenous magnetic field, the permanent magnet having two central holes;

an electronics circuit signal for generating a nuclear magnetic resonance excitation signal and for formulating and analysing the measured signal;

at least one excitation coil connected to the electronic circuit and being disposed within the probe for exposing the fluid sample to the excitation signal and to collect the nuclear magnetic resonance excitation signal; and a catheter extending through the probe from one of the central holes in the permanent magnet to the other one of the central holes in the permanent magnet.

2. A nuclear magnetic resonance spectroscopy catheter probe according to claim 1, further comprising a connection connecting the output of the electronic circuits to an external monitoring unit.

3. A nuclear magnetic resonance spectroscopy catheter probe according to claim 1, wherein the permanent magnet comprises an external cylindrical magnet, and two cylindrical internal permanent magnets disposed within said external cylindrical magnet, each of the magnets having a polarization along its axis of symmetry, the direction of the polarization of the external cylindrical magnet being in the opposed direction of the polarization of the two cylindrical internal permanent magnets.

4. A nuclear magnetic resonance spectroscopy catheter probe according to claim 3, wherein the permanent magnet further comprises two ferrite caps closing the external cylindrical magnet and two magneto concentrators located at the adjacent extremity of the two cylindrical internal permanent magnets.

5. A nuclear magnetic resonance spectroscopy catheter probe according to claim 4, wherein the excitation coil is disposed around a catheter traversing the two cylindrical internal permanent magnets and wherein a pre-processing circuit for detecting and pre-processing the nuclear magnetic resonance signal is located adjacent to the excitation coil.

6. A nuclear magnetic resonance spectroscopy catheter probe according to claim 1, wherein the permanent magnet comprises a cylindrical permanent magnet and wherein at least one excitation coil is disposed in an inner central part of the cylindrical permanent magnet and extends approximately $2/3$ of the length of the cylindrical permanent magnet.

7. A nuclear magnetic resonance spectroscopy catheter probe according to claim 1, wherein the at least one excitation coil is connected to an electronic pre-processing circuit that is disposed adjacent to the coil within the probe.

8. A nuclear magnetic resonance spectroscopy catheter probe according to claim 7, wherein the pre-processing circuit is connected to a printed circuit board that contains the electronic circuits.

9. A nuclear magnetic resonance spectroscopy catheter probe according to claim 3, wherein the two central holes are disposed in the external cylindrical magnet.

10. A nuclear magnetic resonance spectroscopy catheter probe according to claim 4, wherein the two central holes are disposed in the external cylindrical magnet, the catheter extending between the two cylindrical internal permanent magnets.

11. A nuclear magnetic resonance spectroscopy catheter probe according to claim 9, wherein the at least one excitation coil is disposed around the catheter.

12. A nuclear magnetic resonance spectroscopy catheter probe according to claim 10, wherein the at least one excitation coil is disposed around the catheter.

* * * * *